US010570368B2

(12) United States Patent
Shechter et al.

(10) Patent No.: US 10,570,368 B2
(45) Date of Patent: Feb. 25, 2020

(54) FUNCTIONAL SEX-REVERSAL OF DECAPOD CRUSTACEAN FEMALES

(71) Applicant: ENZOOTIC HOLDINGS LTD., Beer Sheva (IL)

(72) Inventors: Assaf Shechter, Tel Aviv (IL); Ohad Rosen, Holon (IL); Amir Sagi, Omer (IL)

(73) Assignee: ENZOOTIC HOLDINGS LTD., Beer Sheva (IL)

(*) Notice: Subject to any disclaimer, the term of this patent is extended or adjusted under 35 U.S.C. 154(b) by 44 days.

(21) Appl. No.: 15/526,212

(22) PCT Filed: Nov. 13, 2015

(86) PCT No.: PCT/IL2015/051096
§ 371 (c)(1),
(2) Date: May 11, 2017

(87) PCT Pub. No.: WO2016/075697
PCT Pub. Date: May 19, 2016

(65) Prior Publication Data
US 2017/0313975 A1    Nov. 2, 2017

Related U.S. Application Data

(60) Provisional application No. 62/079,195, filed on Nov. 13, 2014.

(51) Int. Cl.
| | | |
|---|---|---|
| *A01K 67/02* | (2006.01) | |
| *C12N 5/07* | (2010.01) | |
| *A01K 67/033* | (2006.01) | |
| *C12N 5/071* | (2010.01) | |

(52) U.S. Cl.
CPC ........... *C12N 5/0601* (2013.01); *A01K 67/033* (2013.01); *C12N 5/0683* (2013.01); *A01K 2227/70* (2013.01); *A01K 2267/02* (2013.01); *C12N 2500/02* (2013.01); *C12N 2510/00* (2013.01); *C12N 2517/00* (2013.01)

(58) Field of Classification Search
CPC .......................... C12N 5/0601; C12N 5/0613
USPC ............................................................ 88/20
See application file for complete search history.

(56) References Cited

FOREIGN PATENT DOCUMENTS

WO         0044768 A2     8/2000

OTHER PUBLICATIONS

Manor, 2007, Gen Comp Endocrinol, 150:326-336.*
Ventura, 2011, ISRN Endocrinology, Article 476283, pp. 1-11.*
Rosen, 2010, PLoS ONE, 5(12)e:15281, pp. 1-10.*
Phoungpetchara, 2011, Tissue and Cell, 43:165-171.*
Morakot Sroyrayaa et al., "Bilateral eyestalk ablation of the blue swimmer crab, Portunus pelagicus, produces hypertrophy of the androgenic gland and an increase of cells producing insulin-like androgenic gland hormone", Tissue and Cell 42, R 293-300, 2010.
International Search Report of PCT/IL2015/051096 Completed Feb. 17, 2016; dated Feb. 21, 2016 4 Pages.
Written Opinion of PCT/IL2015/051096 Completed Feb. 17, 2016; dated Feb. 21, 2016 5 Pages.

* cited by examiner

*Primary Examiner* — Valarie E Bertoglio
(74) *Attorney, Agent, or Firm* — The Roy Gross Law Firm, LLC; Roy Gross

(57) ABSTRACT

The present invention provides a primary cell culture which combines a cell culture medium and cells derived from a hypertrophied androgenic gland (AG) of a decapod crustacean. The invention also provides methods for obtaining an all-female progeny by initially injecting/transplanting the primary cell culture to a genetic-female to obtain a male-Neo-male.

5 Claims, 6 Drawing Sheets

US 10,570,368 B2

FUNCTIONAL SEX-REVERSAL OF DECAPOD CRUSTACEAN FEMALES

FIELD OF INVENTION

This invention is directed to; inter alia, cell compositions capable of sex reversal in decapod crustacean females and to a progeny derived, directly or indirectly, from reversed sex decapod crustaceans.

BACKGROUND OF THE INVENTION

The attributes of gender selection in animal breeding and the ability to form an agro-technical infrastructure around it that will improve performance is already well established in cultured animals such as cattle, poultry and fish (De Vries (2008); Correa et al., (2005) and Beardmore et al., (2001)). Crustaceans' aquaculture still predominantly uses heterogenic populations that suppress most sexual dimorphic growth patterns. When segregated, crustaceans demonstrate enhanced growth rates as energy is allocated towards growth rather than towards gonad maturation and other sexual activities related to reproduction. Predominantly, crustacean aquaculture is exclusively depended on nurseries & hatcheries for juvenile supply as reproduction is not part of the grow-out stage in the farm and allocation of energy towards it is undesirable. Thus, culturing of mono-sex populations, either all-male or all-female, produces higher yields and greater commercial value. Although in some crustacean species all-male populations generate higher yields under extensive culturing conditions, several studies suggest (Gopal et al., (2010) and Otoshi et al., (2003)) that under intensified farming conditions and in most decapod crustacean species farmed today it is females that are economically more favorable. In an all-female population under commercial conditions, final sizes at harvest are highly uniform yielding up to 35% higher production value than all-males. Furthermore, it appears that the separation from the males reduces aggressiveness and stress, decreases cannibalism, delivers a higher homogeneity in marketing size and most importantly enables higher stocking rates.

Sexual differentiation and the development of secondary sexual characteristics are controlled by different mechanisms across evolution. In vertebrates and some invertebrate groups, these processes are under the control of sex hormones. Given the recent confirmation that insects probably have no sex hormones, the agents responsible for the sexual maturation of arthropods remain under debate. Crustaceans that are evolutionary close to insects possess an androgenic gland (AG) which is responsible for male sexual differentiation. Interestingly, in some crustaceans, endocrine regulation of sexual differentiation precedes the phenotypic appearance of this secondary external feature.

The role of the AG in male sexual differentiation was demonstrated in several crustacean species by observing primary and secondary sex characteristics after AG removal or transplantation. In the amphipod *Orchestia gamarella*, bilateral AG ablation diminished spermatogenesis and obstructed the development of secondary male characteristics. In *Macrobrachium rosenbergii*, a fully functional sex reversal from males to Neo-females and from females to Neo-males was achieved by surgical bilateral AG ablation and transplantation, respectively.

To date, no effective technology for production of female mono-sex decapod crustacean populations is achieved. There is still a need for efficient, cost-effective and safe methods for production of mono-sex all-female populations of decapod crustaceans.

SUMMARY OF THE INVENTION

In one embodiment, the present invention provides a primary cell culture comprising: cell culture medium and cells derived from a hypertrophied androgenic gland (AG) of a decapod crustacean. In one embodiment, the primary cell culture is devoid of tissue fragments. In one embodiment, hypertrophied AG gland is also a hyperplastic or hyperplasic. In another embodiment, the terms "hyperplasic" and "hyperplastic" are interchangeable.

In another embodiment, the present invention further provides a composition comprising at least $1\times10^2$ solitary cells derived from a hypertrophied androgenic gland (AG) of a decapod crustacean.

In another embodiment, the present invention further provides a process for obtaining a primary cell culture comprising cell culture medium and cells derived from a hypertrophied androgenic gland (AG) of a decapod crustacean, comprising the steps: Obtaining solitary cells by enzymatic dissociation of AG cells from a hypertrophied androgenic gland (AG) of a decapod crustacean; Seeding the disassociated AG cells in a cell culture medium; and incubating the cells from step (b) in a $CO_2$-free incubator at 26° C. to 28° C.; thereby obtaining a primary cell culture to comprising cell culture medium and cells derived from a hypertrophied androgenic gland (AG) of a decapod crustacean.

In another embodiment, the present invention further provides a genetic-female (WZ) decapod crustacean, comprising a primary cell culture. In another embodiment, a genetic-female decapod crustacean, comprising a primary cell culture undergoes a full sex reversal (to male)—Neo-male. In another embodiment, the present invention provides a homogametic WW decapod crustacean.

In another embodiment, the present invention further provides a method for obtaining an all-female progeny, comprising the step of mating WW female with a male (ZZ) decapod crustacean, thereby obtaining an all-female progeny.

In another embodiment, the present invention further provides a method for obtaining a male comprising the W sex chromosome, comprising the step of injecting to a decapod crustacean, younger than 80 days post-larva and comprising the W sex chromosome, a composition comprising at least $1\times10^2$ solitary cells derived from a hypertrophied androgenic gland (AG) of a decapod crustacean, thereby obtaining a heterogametic male bearing the W sex chromosome.

DETAILED DESCRIPTION OF THE INVENTION

Figure 1:
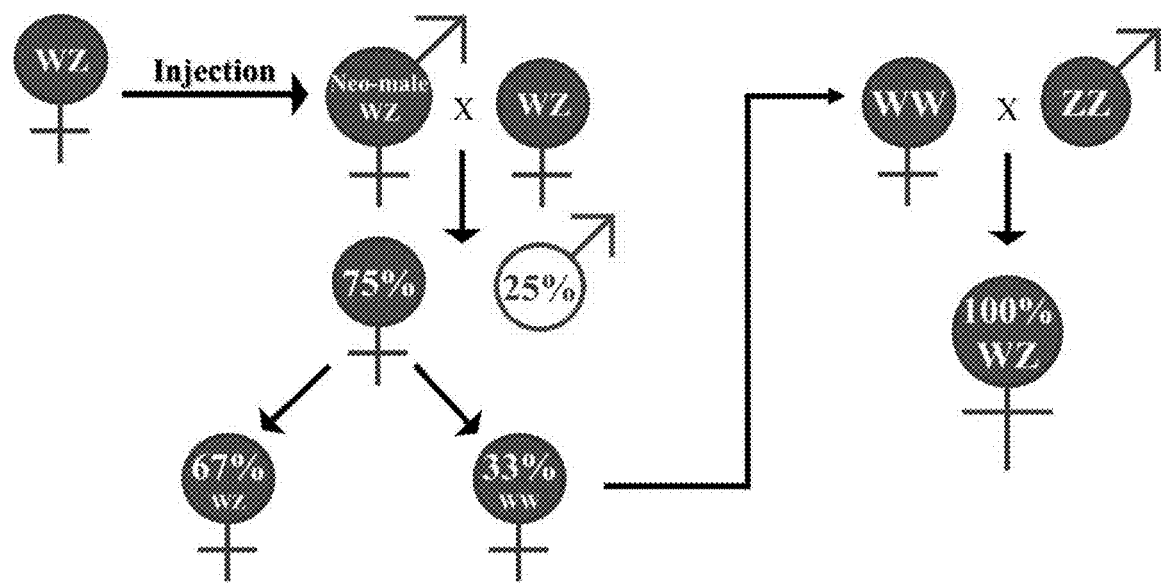
FIG. 1: Schematic sex determination model in the production of Neo-males, WW females and all-female progeny. ♀—represents females and ♂—represents males. The letters W and Z are used to illustrate the chromosome-based sex determination model. WZ and WW are females and ZZ are males. X describes breeding and small arrows point to the progeny of each crossing. Percentages (%) reflect ratios in each progeny comparing males vs. females or normal females (WZ) vs. homogametic females (WW). Injection refers to the administration of enzymatically-dissociated hypertrophied AG cell suspension culture. The large arrow points to the continuation of the diagram to the breeding of WW females.

In one embodiment, the present invention provides a primary cell culture comprising: cell culture medium and cells derived from a hypertrophied androgenic gland (AG) of a decapod crustacean. In another embodiment, "a primary cell culture" is a cell culture derived from an androgenic gland. In another embodiment, "a primary cell culture" according to the invention does not include immortalized cells. In another embodiment, "a primary cell culture" according to the invention does not include transformed cells. In another embodiment, "a primary cell culture" according to the invention does not include neoplastic cells. In another embodiment, a composition of the invention comprises "a primary cell culture". In one embodiment, a decapod crustacean is a Penaeid shrimp decapod crustacean.

In one embodiment, the present invention provides that a decapod crustacean is *Macrobrachium rosenbergii*.

In another embodiment, cells within "a primary cell culture" comprise or consist enzymatically-dissociated hypertrophied androgenic gland cell. In another embodiment, a primary cell culture of the invention is utilized for an unexpectedly robust and successful method for producing a Neo-male decapod crustacean. In another embodiment, injecting a composition of the invention into post-larvae female decapod crustacean results in sex-reversal. In another embodiment, injecting a composition of the invention comprising cells is transplanting cells as described herein. In another embodiment, injecting a composition of the invention comprising cells is transplanting solitary cells. In another embodiment, the source of the cells described herein and the decapod crustacean to be treated with the cells described herein are of the same species. In another embodiment, a post-larvae female decapod crustacean (having female chromosomes composition) which underwent sex reversal to a sexually functional male—termed "Neo-male" is crucial for the later production of mono-sex all-female progeny or culture. In another embodiment, a post-larvae female decapod crustacean as described herein is a wild-type female decapod crustacean.

In another embodiment, at least 40% of the genetic females undergone injection/transplantation of cells as described herein survived this procedure. In another embodiment, at least 50% of the genetic females undergone injection/transplantation of cells as described herein survived this procedure. In another embodiment, at least 60% of the genetic females undergone injection/transplantation of cells as described herein survived this procedure. In another embodiment, at least 70% of the genetic females undergone injection/transplantation of cells as described herein survived this procedure. In another embodiment, at least 75% of the genetic females undergone injection/transplantation of cells as described herein survived this procedure. In another embodiment, at least 80% of the genetic females undergone injection/transplantation of cells as described herein survived this procedure. In another embodiment, according to the present experiment 81% of the genetic females undergone injection/transplantation of cells as described herein survived this procedure (data not shown). In another embodiment, transplantation according to the invention is allogeneic transplantation.

In another embodiment, at least 40% to 90% of the genetic females undergone injection of cells as described herein survived this procedure. In another embodiment, at least 50% to 80% of the genetic females undergone injection/transplantation of cells as described herein survived this procedure. In another embodiment, at least 60% to 80% of the genetic females undergone injection/transplantation of cells as described herein survived this procedure.

In another embodiment, at least 25% of the genetic females undergone injection/transplantation of cells as described herein developed into Neo-males. In another embodiment, a "Neo-male" is a genetic female having the capability of fertilizing eggs. In another embodiment, having the capability of fertilizing eggs is having the capability to mate with a female decapod crustacean as described herein. In another embodiment, a "Neo-male" is a genetic female having the capability of fertilizing eggs upon sexual maturity into a male. In another embodiment, a "Neo-male" is a genetic female comprising Appendix masculina (AM). In another embodiment, a "Neo-male" is a genetic female comprising at least one male gonopore. In another embodiment, a "Neo-male" is a genetic female comprising Appendix masculina (AM), at least one male gonopore and having the capability of fertilizing eggs upon sexual maturity. In another embodiment, at least 30% of the genetic females undergone injection/transplantation of cells as described herein developed into Neo-males. In another embodiment, at least 35% of the genetic females undergone injection/transplantation of cells as described herein developed into Neo-males. In another embodiment, at least 40% of the genetic females undergone injection/transplantation of cells as described herein developed into Neo-males. In another embodiment, at least 45% of the genetic females undergone injection/transplantation of cells as described herein developed into Neo-males. In another embodiment, at least 50% of the genetic females undergone injection/transplantation of cells as described herein developed into Neo-males. In another embodiment, at least 60% of the genetic females undergone injection/transplantation of cells as described herein developed into Neo-males. In another embodiment, at least 70% of the genetic females undergone injection/transplantation of cells as described herein developed into Neo-males. In another embodiment, at least 80% of the genetic females undergone injection/transplantation of cells as described herein developed into Neo-males. In another embodiment, at least 90% of the genetic females undergone injection/transplantation of cells as described herein developed into Neo-males.

In another embodiment, 25% to 90% of the genetic females undergone injection/transplantation of cells as described herein developed into Neo-males. In another embodiment, 25% to 60% of the genetic females undergone injection/transplantation of cells as described herein developed into Neo-males. In another embodiment, 25% to 50% of the genetic females undergone injection/transplantation of cells as described herein developed into Neo-males.

In another embodiment, mating a Neo-male with a normal female resulted in a progeny comprising at least 500 individual WW females. In another embodiment, mating a Neo-male with a normal female resulted in a progeny comprising at least 600 individual WW females. In another embodiment, mating a Neo-male with a normal female resulted in a progeny comprising at least 700 individual WW females. In another embodiment, mating a Neo-male with a normal female resulted in a progeny comprising at least 800 individual WW females. In another embodiment, mating a Neo-male with a normal female resulted in a progeny comprising at least 900 individual WW females. In another embodiment, mating a Neo-male with a normal female resulted in a progeny comprising at least 1000 individual WW females. In another embodiment, mating a Neo-male with a normal female resulted in a progeny comprising 150 to 1,500 individual WW females. In another embodiment, mating a Neo-male with a normal female resulted in a progeny comprising 200 to 2,000 individual WW females. In another embodiment, mating a Neo-male with a normal female resulted in a progeny comprising 250 to 2,500 individual WW females. In another embodiment, the number of WW offspring was determined based on multiple sampling of multiple crossings (data not shown).

In another embodiment, a "Neo-male" is a decapod crustacean Neo-male. In another embodiment, a "male" is a decapod crustacean male. In another embodiment, a "female" is a decapod crustacean female.

In another embodiment, the present invention provides a method for generating a WW female. In another embodiment, a WW female cannot be a product of nature in species where intersexuality is unnatural. In another embodiment, the present invention provides a WW female. In another embodiment, the present invention provides a method for generating a WW female comprising crossing a WZ Neo-male (a manipulated sexually reversed female) with a normal female or a WZ female. In another embodiment, the present invention provides that WZ Neo-male are brothers (offspring of a single crossing between Normal ZZ male and WZ female- P generation). In another embodiment, W or Z refers to the sex chromosome or a gamete of a decapod crustacean as described herein. In another embodiment, WW, WZ or ZZ refers to the genotypic sex of a decapod crustacean as described herein.

In another embodiment, Neo-males are produced by manipulating the progeny resulting from crossing sexually matured male (ZZ) and female (WZ) of the decapod crustacean (P crossing). In another embodiment, the post larvae (PL) progeny of male (ZZ) and female (WZ) crossing is comprised of about 50% males and about 50% females (progeny of P crossing). In another embodiment, female PLs derived from progeny of P crossing were segregated from males. In another embodiment, female PLs derived from progeny of P crossing were segregated from males by means of molecular genetic sex determination using a W-specific DNA sex marker.

In another embodiment, prior to $PL_{120}$, identified female PLs derived from progeny of P crossing were manipulated by injecting a composition comprising cells as described herein for obtaining WZ Neo-males. In another embodiment, WZ Neo-males were grown until male-specific secondary sexual characteristics such as development of Appendix masculina (AM) and gonopores at the base of the fifth walking legs were verified.

In another embodiment, a sexually mature WZ Neo-male was crossed with a wild-type female or a WZ female (F1 crossing). In another embodiment, the progeny of this F1 cross yielded about 3:1 female to male sex ratio. In another embodiment, ZZ male progeny of this F1 crossing were excluded and of the remaining females progeny of this F1 crossing, about 33% were WW females. In another embodiment, using the W-specific DNA sex marker ZZ males progeny of this F1 crossing were excluded and of the remaining females progeny of this F1 crossing, about 33% were identified as WW by using a negative screen based on a Z-specific DNA sex marker.

In another embodiment, 2 to 250 siblings having 2 types of gametes, ~50% bearing the W sex chromosome and ~50% bearing the Z sex chromosome of the F1 generation are randomly chosen for sex-reversal manipulation. In another embodiment, at least about 50% of the siblings having 2 types of gametes, ~50% bearing the W sex chromosome and ~50% bearing the Z sex chromosome of the F1 generation that were randomly chosen for sex-reversal manipulation actually mature into Neo-males. In another embodiment, Neo-males (sibling) that were grown to sexual maturity were further crossed with normal WZ females. In another embodiment, provided herein a method for obtaining a WW female comprising crossing Neo-males with normal WZ females (F2 progeny).

In another embodiment, F2 progeny (the progeny of Neo-males and WZ females) gave rise to at least 500 WW females. In another embodiment, F2 progeny (the progeny of Neo-males and WZ females) gave rise to at least 700 WW females. In another embodiment, F2 progeny (the progeny of Neo-males and WZ females) gave rise to at least 900 WW females. In another embodiment, F2 progeny (the progeny of Neo-males and WZ females) gave rise to at least 1,000 WW females. In another embodiment, F2 progeny (the progeny of Neo-males and WZ females) gave rise to 200 to 2,000 WW females. In another embodiment, F2 progeny (the progeny of Neo-males and WZ females) gave rise to 250 to 2,500 WW females. In another embodiment, F2 progeny (the progeny of Neo-males and WZ females) gave rise to at least 1200 WW females. In another embodiment, at least five WW females are cousins. In another embodiment, the cousins WW females are produced from crossings involving five different Neo-males, wherein the Neo-males are brothers originating from the same parents.

In another embodiment, all cells within the primary cell culture are cells derived from a hypertrophied androgenic gland (AG) of a decapod crustacean. In another embodiment, the primary cell culture is a "hypertrophied androgenic gland primary cell culture".

In another embodiment, at least 50% of the cells within the primary cell culture and/or the composition as described herein are endocrine AG cells. In another embodiment, at least 60% of the cells within the primary cell culture and/or the composition as described herein are endocrine AG cells. In another embodiment, at least 65% of the cells within the primary cell culture and/or the composition as described herein are endocrine AG cells. In another embodiment, at least 70% of the cells within the primary cell culture and/or the composition as described herein are endocrine AG cells. In another embodiment, at least 75% of the cells within the primary cell culture and/or the composition as described herein are endocrine AG cells. In another embodiment, at least 80% of the cells within the primary cell culture and/or the composition as described herein are endocrine AG cells. In another embodiment, at least 85% of the cells within the primary cell culture and/or the composition as described herein are endocrine AG cells. In another embodiment, at least 90% of the cells within the primary cell culture and/or the composition as described herein are endocrine AG cells. In another embodiment, at least 95% of the cells within the primary cell culture and/or the composition as described herein are endocrine AG cells. In another embodiment, at least 98% of the cells within the primary cell culture and/or the composition as described herein are endocrine AG cells. In another embodiment, at least 99% of the cells within the primary cell culture and/or the composition as described herein are endocrine AG cells.

In another embodiment, endocrine AG cells produce at least one factor. In another embodiment, endocrine AG cells express and/or produce factors that induce sexual differentiation. In another embodiment, endocrine AG cells express and/or produce at least one factor that induces development of male sexual characters. In another embodiment, endocrine AG cells express and/or produce an AG specific insulin-like encoding transcript (IAG) and/or protein. In another embodiment, endocrine AG cells express and/or produce a protein belonging to the insulin family of hormones. In another embodiment, endocrine AG cells express and/or produce multiple factors that induce development of male sexual characters. In another embodiment, endocrine AG cells are part of an endocrine axis which controls sex differentiation, development and maintenance of male sexual characters.

In another embodiment, at least 8% of the cells within the primary cell culture and/or the composition as described herein are solitary cells. In another embodiment, at least 10% of the cells within the primary cell culture and/or the composition as described herein are solitary cells. In another embodiment, at least 20% of the cells within the primary cell culture and/or the composition as described herein are solitary cells. In another embodiment, at least 25% of the cells within the primary cell culture and/or the composition as described herein are solitary cells. In another embodiment, at least 30% of the cells within the primary cell culture and/or the composition as described herein are solitary cells. In another embodiment, at least 35% of the cells within the primary cell culture and/or the composition as described herein are solitary cells. In another embodiment, at least 40% of the cells within the primary cell culture and/or the composition as described herein are solitary cells. In another embodiment, at least 45% of the cells within the primary cell culture and/or the composition as described herein are solitary cells. In another embodiment, at least 50% of the cells within the primary cell culture and/or the composition as described herein are solitary cells. In another embodiment, at least 60% of the cells within the primary cell culture and/or the composition as described herein are solitary cells. In another embodiment, at least 70% of the cells within the primary cell culture and/or the composition as described herein are solitary cells. In another embodiment, at least 80% of the cells within the primary cell culture and/or the composition as described herein are solitary cells. In another embodiment, at least 90% of the cells within the primary cell culture and/or the composition as described herein are solitary cells. In another embodiment, at least 95% of the cells within the primary cell culture and/or the composition as described herein are solitary cells.

In another embodiment, at least 8% of the cells within the primary cell culture and/or the composition as described herein are aggregated. In another embodiment, at least 10% of the cells within the primary cell culture and/or the composition as described herein are agglomerate. In another embodiment, at least 20% of the cells within the primary cell culture and/or the composition as described herein are agglomerate. In another embodiment, at least 25% of the cells within the primary cell culture and/or the composition as described herein are agglomerate. In another embodiment, at least 30% of the cells within the primary cell culture and/or the composition as described herein are aggregate. In another embodiment, at least 35% of the cells within the primary cell culture and/or the composition as described herein are aggregate. In another embodiment, at least 40% of the cells within the primary cell culture and/or the composition as described herein are aggregate. In another embodiment, at least 45% of the cells within the primary cell culture and/or the composition as described herein are aggregate. In another embodiment, at least 50% of the cells within the primary cell culture and/or the composition as described herein are aggregate. In another embodiment, at least 60% of the cells within the primary cell culture and/or the composition as described herein are aggregate. In another embodiment, at least 70% of the cells within the primary cell culture and/or the composition as described herein are aggregate.

In another embodiment, an aggregate of cells of the invention comprises 2 to 70 cells. In another embodiment, an aggregate of cells of the invention comprises 2 to 50 cells. In another embodiment, an aggregate of cells of the invention comprises 2 to 40 cells. In another embodiment, an aggregate of cells of the invention comprises 2 to 30 cells. In another embodiment, an aggregate of cells of the invention comprises 2 to 25 cells. In another embodiment, an aggregate of cells of the invention comprises 2 to 20 cells.

In another embodiment, the primary cell culture and/or the composition as described herein is devoid or substantially devoid of an intact tissue. In another embodiment the primary cell culture and/or the composition as described herein is devoid or substantially devoid of tissue fragments.

In another embodiment, a hypertrophied AG gland is also a hyperplastic/hyperplasic AG gland. In another embodiment, a hypertrophied AG gland is a gland which its volume was increased. In another embodiment, a hypertrophied AG gland is a gland which its volume was increased by artificial means. In another embodiment, a hypertrophied AG gland is a gland with enlarged (compared to a normal, gland) component cells. In another embodiment, a hyperplasic AG gland is characterized by an increased number of cells (compared to normal gland).

In another embodiment, a primary cell culture and/or a composition as described herein comprises at least $1 \times 10^2$ cells or solitary cells derived from a hypertrophied androgenic gland (AG) of a decapod crustacean. In another embodiment, a primary cell culture and/or a composition as described herein comprises at least $1 \times 10^3$ cells or solitary cells derived from a hypertrophied androgenic gland (AG) of a decapod crustacean. In another embodiment, a primary cell culture and/or a composition as described herein comprises at least $1 \times 10^4$ cells or solitary cells derived from a hypertrophied androgenic gland (AG) of a decapod crustacean. In another embodiment, a primary cell culture and/or a composition as described herein comprises at least $1 \times 10^5$ cells or solitary cells derived from a hypertrophied androgenic gland (AG) of a decapod crustacean. In another embodiment, a primary cell culture and/or a composition as described herein comprises at least $1 \times 10^6$ cells or solitary cells derived from a hypertrophied androgenic gland (AG) of a decapod crustacean. In another embodiment, a primary cell culture and/or a composition as described herein comprises at least $1 \times 10^7$ cells or solitary cells derived from a hypertrophied androgenic gland (AG) of a decapod crustacean. In another embodiment, a primary cell culture and/or a composition as described herein comprises at least $1 \times 10^8$ cells or solitary cells derived from a hypertrophied androgenic gland (AG) of a decapod crustacean.

In another embodiment, a composition as describe herein comprises cell culture medium. In another embodiment, cell culture medium supports the growth of the cells described herein. In another embodiment, cell culture medium supports the proliferation of the cells described herein. In another embodiment, cell culture medium induces or maintains androgenic hormone secretion by the cells described herein. In another embodiment, suitable cell culture mediums are known to one of skill in the art.

In another embodiment, a composition as describe herein comprises: Arginine, biotin, NaCl, glucose, insulin, Cystine, choline, KCl, penicillin, transferring, Glutamine, folate, $NaH_2PO_4$, streptomycin specific growth factors, Histidine nicotinamide, $NaHCO_3$, phenol red, Isoleucine, pantothenate, $CaCl_2$, whole serum, Leucine, pyridoxal, $MgCl_2$, Lysine, thiamine, Methionine, riboflavin, Phenylalanine, Threonine, Trytophan, Tyrosine, Valine or any combination thereof.

In another embodiment, suitable cell culture medium comprises L-15. In another embodiment, suitable cell culture medium comprises buffered L-15. In another embodiment, suitable cell culture medium comprises one or more free base amino acid. In another embodiment, suitable cell culture medium comprises L-Glutamine. In another embodiment, suitable cell culture medium comprises serum. In another embodiment, suitable cell culture medium comprises fetal bovine serum. In another embodiment, suitable cell culture medium comprises an antibiotic or a combination of antibiotic such as but not limited to Penicillin-Streptomycin.

Process

In another embodiment, provided herein a method for obtaining enzymatically-dissociated hypertrophied androgenic gland (AG) primary cell culture in suspension from decapod crustaceans. In another embodiment, the invention provides a process for obtaining a primary cell culture, wherein the primary cell culture comprises/consists cells derived from a hypertrophied androgenic gland (AG) of a decapod crustacean and medium, comprising the steps: (a) Obtaining solitary cells by enzymatically-dissociating AG cells from a hypertrophied androgenic gland (AG) of a decapod crustacean; (b) Seeding the disassociated AG cells in a cell culture medium; and (c) Incubating the cells from step (b) in an incubator at 25° C. to 27° C.; thereby obtaining a primary cell culture comprising cell culture medium and cells derived from a hypertrophied androgenic gland (AG) of a decapod crustacean. In another embodiment, an incubator is a $CO_2$-free incubator. In another embodiment, the incubator's temperature is about 26° C.

Sexually Reversed Decapods

In another embodiment, the present invention provides a decapod crustacean, comprising the primary cell culture and/or the composition as described herein. In another embodiment, the present invention provides a female decapod crustacean, comprising the primary cell culture and/or the composition as described herein. In another embodiment, a decapod crustacean or a female decapod crustacean is up to 180 days post-larvae old decapod crustacean. In another embodiment, the present invention provides a female decapod crustacean undergoing sex reversal, comprising the primary cell culture and/or the composition as described herein. In another embodiment, the female decapod crustacean that underwent sex reversal according to the present invention provides an offspring. In another embodiment, the female decapod crustacean that underwent sex reversal according to the present invention provides a homogametic WW decapod crustacean offspring.

In another embodiment, the present invention provides a method for obtaining an all-female progeny, comprising the step of mating a homogametic WW female with a male decapod crustacean, thereby obtaining an all-female progeny. In another embodiment, the present invention provides a method for obtaining an all-female progeny, comprising the step of mating a homogametic WW female with a heterogametic male decapod crustacean, thereby obtaining an all-female progeny. In another embodiment, the present invention provides a method for obtaining an all-female progeny, comprising the step of mating a homogametic WW female with a homogametic male decapod crustacean, thereby obtaining an all-female progeny. In another embodiment, a homogametic WW female is an offspring of the female decapod crustacean that underwent sex reversal according to the present invention.

In another embodiment, the present invention provides a method for obtaining a male having the W sex chromosome, comprising the step of injecting to a decapod crustacean comprising the W sex chromosome and younger than 180 days post-larva, a composition comprising at least $1 \times 10^2$ solitary cells derived from a hypertrophied androgenic gland (AG) of a decapod crustacean, thereby obtaining a male having the W sex chromosomes. In another embodiment, the present invention provides a method for obtaining a male having the W sex chromosome (genetically a female), comprising the step of injecting to a genetically female decapod crustacean (comprising the W sex chromosome) younger than 180 days post-larva, a composition comprising at least $1 \times 10^2$ solitary cells derived from a hypertrophied androgenic gland (AG) of a decapod crustacean.

In another embodiment, younger than 180 days post-larva is younger than 160 days post-larva. In another embodiment, younger than 180 days post-larva is younger than 150 days post-larva. In another embodiment, younger than 180 days post-larva is younger than 130 days post-larva. In another embodiment, younger than 180 days post-larva is younger than 120 days post-larva. In another embodiment, younger than 180 days post-larva is younger than 100 days post-larva. In another embodiment, younger than 180 days post-larva is younger than 80 days post-larva. In another embodiment, younger than 180 days post-larva is younger than 60 days post-larva. In another embodiment, younger than 180 days post-larva is 1-60 days post-larva. In another embodiment, younger than 180 days post-larva is younger than 30 days post-larva.

In another embodiment, injecting is injecting into the muscular tissue of an abdominal segment. In another embodiment, injecting is injecting into the muscular tissue of the first abdominal segment. In another embodiment, injecting is injecting into the muscular tissue of the second abdominal segment.

In another embodiment, provided herein a method for injection of enzymatically-dissociated hypertrophied AG primary cell culture in suspension in decapod crustaceans. In another embodiment, provided herein a method for production of Neo-male decapod crustaceans by injection of dissociated hypertrophied AG cells obtained from primary culture in suspension—the composition. In another embodiment, provided herein a method for production of Neo-male decapod crustaceans by a single injection of dissociated hypertrophied AG cells obtained from primary culture in suspension.

In another embodiment, the hypertrophied cells are obtained from a hypertrophied AG of an adult male decapod crustacean following at least 5 days from bi-lateral surgical removal of the X-organ Sinus-gland complex. In another embodiment, the hypertrophied cells are obtained from a hypertrophied AG of an adult male decapod crustacean following at least 8 days from bi-lateral surgical removal of the X-organ Sinus-gland complex. In another embodiment, the hypertrophied cells are obtained from a hypertrophied AG of an adult male decapod crustacean following any known treatment that can induce hypertrophy in an AG. In another embodiment, the hypertrophied cells are obtained from a hypertrophied AG of an adult male decapod crustacean following 4-15 days from bi-lateral surgical removal of the X-organ Sinus-gland complex.

In another embodiment, provided herein the composition described herein is injected once or more into a female decapod crustacean at the age range from 1 to 100 days post-larvae. In another embodiment, provided herein the composition described herein is injected once or more into a female decapod crustacean at the age range from 1 to 50 days post-larvae. In another embodiment, injection is by means of a micro-injector apparatus. In another embodiment, injection to a sexually immature female induces functional sex reversal to male and/or Neo-male. The latter male and/or Neo-male is used, in some embodiments, to obtain all-female mono-sex population by producing WW females.

As used herein, the singular forms "a", "an", and "the" include plural forms unless the context clearly dictates otherwise. Thus, for example, reference to "a therapeutic agent" includes reference to more than one therapeutic agent.

Unless specifically stated or obvious from context, as used herein, the term "or" is understood to be inclusive.

The term "including" is used herein to mean, and is used interchangeably with, the phrase "including but not limited to".

As used herein, the terms "comprises," "comprising," "containing," "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

In some embodiments, a composition of the invention comprises pharmaceutically active agents. In some embodiments, pharmaceutically active agents are added prior to transplantation. Pharmaceutically active agents include but are not limited to any of the specific examples disclosed herein. Those of ordinary skill in the art will recognize also numerous other compounds that fall within this category and are useful according to the invention.

As used herein, "an effective amount" refers to that amount of cells that produces the desired effect (such as treatment or sex-reversal).

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about .

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Material and Methods

Animals

*Macrobrachium rosenbergii* blue claw males (40±5 g) were reared in separate 600 L tanks at 28±2° C. with constant aeration, light regime of 14:10 (L:D) and fed ad libitum (shrimp pellets comprising 30% protein) in the facilities of Enzootic Holdings Ltd. *M. rosenbergii* young individuals post metamorphosis (i.e., post larvae (PL)) were reared in a 3.5 cubic meter U-shaped tank, and maintained as above.

Androgenic Gland Hypertrophy and Enzymatic Cell Dissociation

The neuroendocrine X-organ Sinus-gland complex, located in the eyestalk, is known to secrete neuropeptides which negatively regulate the androgenic gland (AG) and its activities. Thus, an endocrine manipulation which involves its elimination via surgical removal and induces both hypertrophy and hyperplasia of the AG was applied to the *M. rosenbergii* blue claw males. Eight days post the endocrine manipulation; the induced males were anesthetized for 15 minutes in ice cold water supplemented with 0.2% hypochlorite for disinfection purposes. Thereafter, animals were dissected and their hypertrophied AGs were isolated under dissecting light microscope. Subsequently, cells were separated by means of enzymatic dissociation. Briefly, all hypertrophied AGs were pooled into a single tube and were placed on ice. Thereafter, 1 ml of a specific enzyme mix and antibiotics [Leibovitz L-15 Medium with L-Glutamine, 0.1% weight/volume (w/v) Collagenase type I, 0.1% (w/v) Collagenase type IV and Penicillin-Streptomycin Solution] were added. The dissociation reaction tube was then placed in a rotator at a speed of 25 RPM for 40 minutes at room temperature (RT) and followed by a centrifugation at 500×g for 5 minutes, also at RT. Upon centrifugation, the tube was placed in a sterilized biological laminar flow hood. The upper phase (does not include living cells) was removed and the cell pellet was washed by re-suspending it in 1 ml of feeding media [Leibovitz L-15 Medium with L-Glutamine, 10% volume/volume (v/v) fetal bovine serum and Penicillin-Streptomycin Solution] and subsequent centrifugation at 500×g for 5 minutes at RT. Washing procedure was repeated three times. Finally, cells were re-suspended in 500 μl of feeding media.

Cell Counting

Cell concentration and viability were measured using standard Trypan blue stain. Briefly, cells were stained with Trypan blue solution at a final concentration of 0.08% and then loaded to a hemocytometer for observation under a light microscope at a magnification of ×100.

AG Primary Cell Culture

Fractions of 10 μl of the suspended cells in the media were either immediately seeded in a 24-well plate coated with 20 μg/ml poly D-lysine (PDL) at a density of ~1×10$^4$ cells per well or first loaded into a micro-injector apparatus, passed through the micro-injector glass capillary into a 1.5 ml tube and then seeded in a 24-well plate at a density of ~1×10$^4$ cells per well. Of the collected cells, a fraction was allocated for viability assessment and stained as described above. The cells were grown in a $CO_2$-free incubator at 27° C. Twenty four hours after seeding and onwards, the growing media was partially replaced every other day. Overall, cells were maintained for 21 days during which they were monitored under an inverted light microscope and their morphology, density and interactions were documented.

Injection of Hypertrophied AG Cell Suspension into PLs

The ability of the purified and grown hypertrophied AG cells to induce sex reversal was examined. Mixed population (males and females) of PL 60 or 30 days or less ($PL_{\leq 60}$, $PL_{\leq 30}$; n=913) were injected with ~2×10$^3$ hypertrophied AG cells. In general, each PL was restrained on a plasticine surface and using the micro-injector apparatus, while observing through a laboratory binocular, the hypertrophied AG cells from the primary culture were suspended and administrated via a single injection into the muscular tissue of the first abdominal segment. Thereafter, the injected PLs were divided into two groups: (1) Comprising the majority of PLs (n=883) which were kept in either a U-shaped tank of 3.5 cubic meters or a circular tank of ~10 cubic meters or a rectangular (~250 m$^2$; ~8 m×30 m) earthen pond with a water depth of 1 m for grow-out. (2) Comprising representative PLs (n=30) which were kept in a 3.5 cubic meter U-shaped tank. The latter PLs were routinely examined and followed-up for sex reversal into suspected Neo-males.

Appendix Masculina (AM) and Male Gonopores Examination

To evaluate masculine features, the 2$^{nd}$ pleopod (swimming leg) was removed using fine tweezers and the presence/or lack of the AM was confirmed under a light microscope. In mature Neo-males (1 year of age) a regeneration assay was performed. Briefly, Neo-males with confirmed AM, as described above, were allowed to molt and the regeneration of AM was examined.

The appearance of male gonopores at the base of the 5$^{th}$ pereiopods (walking leg) were examined by placing the PL on its dorsal side and viewing under a laboratory binocular.

Molecular Analysis

The 2$^{nd}$ pleopods previously removed for AM observation had been used for genomic DNA (gDNA) extraction for the genetic determination of sex. Briefly, gDNA was extracted using the REDExtract-N-Amp Tissue PCR Kit (Sigma, Israel) and used as a template for PCR of either a W- or Z-specific DNA sex markers (Ventura et al., 2011). PCR products were separated on a 2% agarose gel, stained with Ethidium Bromide and visualized on a UV table.

Histology

Testes were dissected out together with the proximal sperm duct ('vas deferens') from Neo-males (1 year of age). Tissue samples were fixed in modified Carnoy's II [Ethanol 60% (v/v; Bio-Lab Ltd, Israel), Chloroform 30% (v/v; Frutarom, Israel), Glacial acetic acid 10% (v/v; Sigma, Israel) and Formaldehyde 2% (v/v; Sigma, Israel) for 24 h, dehydrated gradually through a series of increasing alcohol concentrations up to Xylen (Sigma, Israel) and embedded in Paraplast (Kendall, Mansfield, Mass.) according to conventional procedures. Sections of 5 μm were cut onto silane-coated slides (Menzel-Gläser, Braunschweig, Germany). Consecutive sections were stained using standard Hematoxylin (Bar Naor, Israel) and Eosin (Bar Naor, Israel) for morphological observations.

Example 1

Production of Neo-Males Using a Single Injection of the Cell Suspension into Post Larvae Female Decapod Crustacean The experimental data provided herein demonstrates the ability to produce an enzymatically-dissociated decapod crustaceans hypertrophied androgenic gland primary cell culture in suspension and the utilization of the decapod crustaceans hypertrophied androgenic gland primary cell culture for the production of Neo-males. These Neo-males are further utilized for mating and producing a WW females resulting in the generation of a mono-sex all-female culture-progeny.

W and Z Chromosomes—Sex Determination

The schematic flow diagram presented in FIG. 1 illustrates the W and Z chromosome-based sex determination model. According to this genetic mode of inheritance, females are heterogametic (WZ) and males are homogametic (ZZ). The diagram highlights that even a single injection of hypertrophied AG primary cell culture in suspension to young decapod crustacean female PLs can induce a full and functional sex reversal into a Neo-male. Unexpectedly, this manipulation did not cause any illnesses or death to the treated animals. It is important to emphasize the present invention overcomes the hurdles associated with AG tissue implantation which resulted in devastating death rate and low sex reversal rate.

The "produced" Neo-males, which are fully sexually functional as males, are genetic females bearing a W gamete. Upon a successful mating of a Neo-male (WZ) with a normal female (such as WZ), 25% of the progeny were found to be males (ZZ) and the remaining 75% were females. Out of the latter, 67% were identified as normal heterogametic (WZ) females while the remaining 33% were found to be unique WW homogametic females.

Further mating these WW homogametic females with males gave rise to a 100% WZ heterogametic female progeny.

As a prerequisite to obtain a suspensible hypertrophied androgenic gland cell culture, adult male decapod crustaceans must be endocrinologically-induced so the levels of specific AG-inhibiting neuropeptides are decreased and the gland produces sufficient amounts of androgenic hormones that can actually induce development of male in an animal capable of developing to both male and female (regardless of the composition of its sex chromosomes). This intervention, in turn, leads to the hypertrophy of the AG and its comprising cells.

Figure 2:
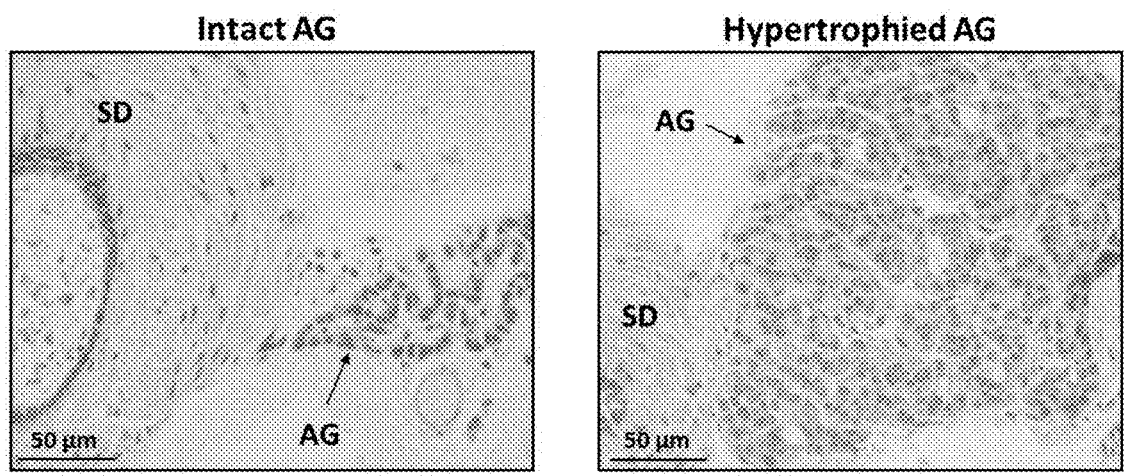
FIG. 2: A micrograph of a histological comparison of intact and hypertrophied androgenic glands of *M. rosenbergii*. (A) Sections of an intact androgenic gland (AG) and (B) a hypertrophied AG which were stained using hematoxylin and eosin and observed under light microscope. The location of the AG is pointed out (arrows). Sperm Duct (SD). Scale bar represents 50 μm.

Histological comparisons between intact AG (FIG. 2A) and a hypertrophied AG (FIG. 2B) clearly demonstrate the substantial differences in the total size of the AG, the number of cells comprising it and their characterization. Surgically removed hypertrophied AGs were dissociated using a specific enzymatic mixture to obtain a suspension of individual cells.

The passage through the micro-injector did not seem to have an apparent effect on the viability of the AG cells. The seeded primary cell culture was documented on days 2 and 6 (FIG. 3A and 3B, respectively), and was found to be viable for as long as 21 days in culture.

Figure 3:
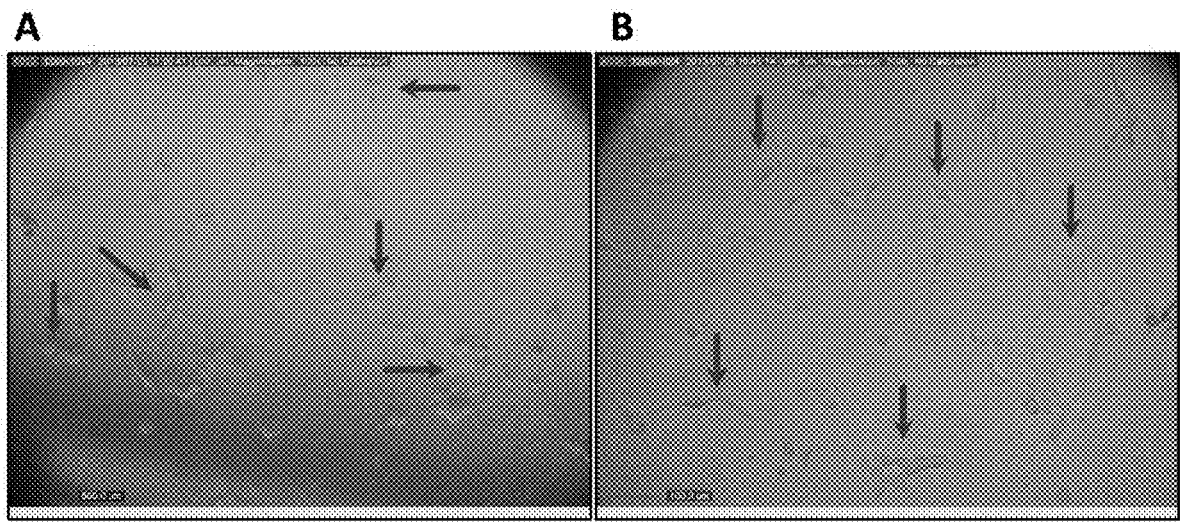
FIG. 3: A micrograph of an enzymatically-dissociated hypertrophied AG primary cell culture in suspension from *M. rosenbergii* across time. AG cells were documented (A) 2 days and (B) 6 days after being seeded using inverted light microscope. The location of the AG cells in the culture is pointed out (arrow). Scale bar represents 500 μm in (A) and 100 μm in (B).

Light microscope images of the culture highlighted the viability of cells, demonstrating well-developed cell extensions (FIG. 3). The Latter are hallmark characterizations of a healthy living primary culture, as oppose to dead cells which tend to shrink and subsequently detach from the well surface and float.

Figure 4:
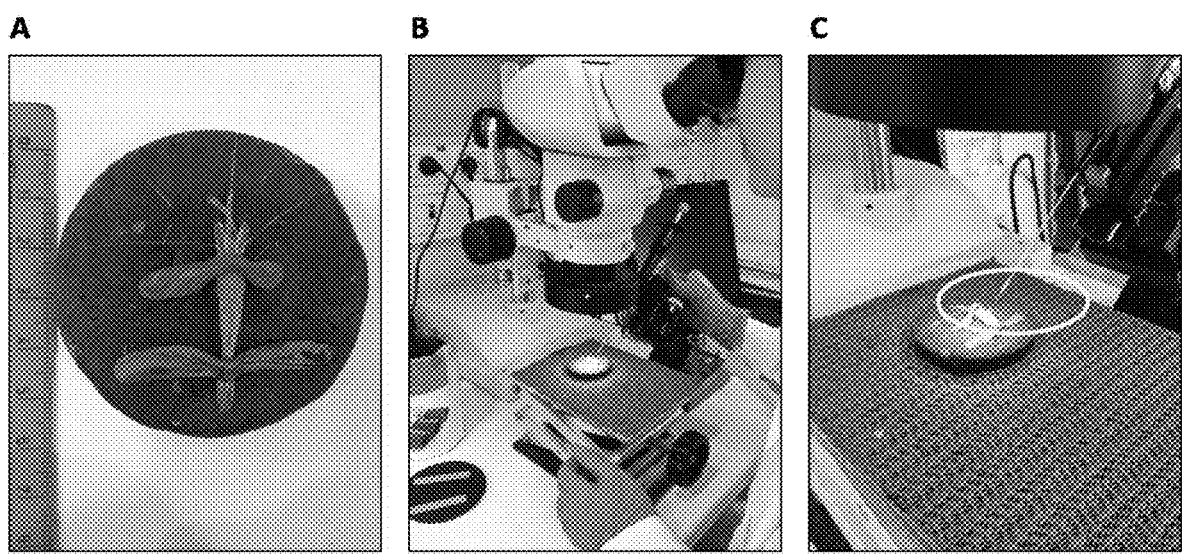
FIG. 4: Micrographs showing injection of enzymatically-dissociated hypertrophied primary AG cell culture in suspension using a micro-injector apparatus to post larvae *M. rosenbergii* females. (A) A post larvae is first restrained on a plasticine surface before (B) being placed under a laboratory binocular for the operation of a micro-injector. (C) The insertion of a glass capillary (highlighted by circle) of the micro-injector (top side of the image) in the injection procedure of the cell suspension.

In order to inject the cell suspension to very small PLs, at early ages as 20 to 60 days or less post metamorphosis (termed $PL_{\leq 60}$), a specialized infrastructure combining a micro-injector apparatus and a laboratory binocular, was assembled (FIG. 4). The manipulation was performed on each restrained animal under a laboratory binocular using a micro-injector apparatus (FIG. 4).

A total of 450 female PLs were injected once with hypertrophied AG primary cell culture suspension. The direct mortality caused by the manipulation was recorded immediately post manipulation and up to 48 hours. The PL immediate survival rate was found to be high, standing at 81%.

Figures 5, 6:
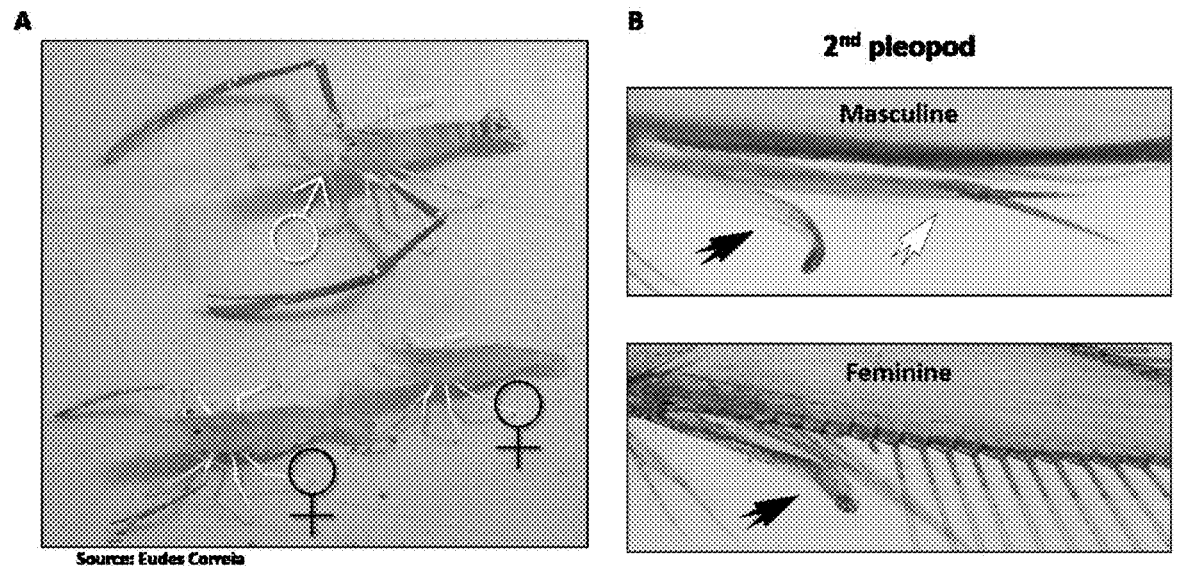
FIG. 5: Micrographs showing external secondary sex characters in *M. rosenbergii*. (A) Image of a male (♂) and two females (♀)—source: Eudes Correia. (B) Dissecting microscope images of the $2^{nd}$ pleopod of a male (top image) and female (bottom image) *M. rosenbergii*. The masculine pleopod contains both appendix masculina (white arrow) and appendix interna (black arrow) while the feminine pleopod contains only appendix interna.
FIG. 6: A gel micrograph showing genetic sex determination of suspected Neo-male PLs. To discriminate the morphologically-indistinguishable males from Neo-males, all the representative PLs which were manipulated by injection and examined for the development (✓) or lack of (x) AM and masculine gonopores, were genetically examined using a female-specific DNA sequence. The latter was amplified by means of PCR and was separated through a 2% agarose gel stained by Ethidium Bromide and visualized using UV (upper panel). Mr β-actin served as a positive control for PCR, ensuring the presence of DNA in each sample (lower panel). DNA of a true *M. rosenbergii* female (♀) and water served as a positive and negative control (NC), respectively.

When reaching sexual maturity, *M. rosenbergii* demonstrates clear sexual dimorphism and males are highly distinct from females (FIG. 5A). Prior to full sexual maturity, male-specific secondary sex characteristic—AM, can be detected on the $2^{nd}$ pleopod of males when observed under a laboratory binocular (FIG. 5B, upper panel). This is in contrast to the appendix interna, which is observed in both males and females (FIG. 5B).

Figure 7:
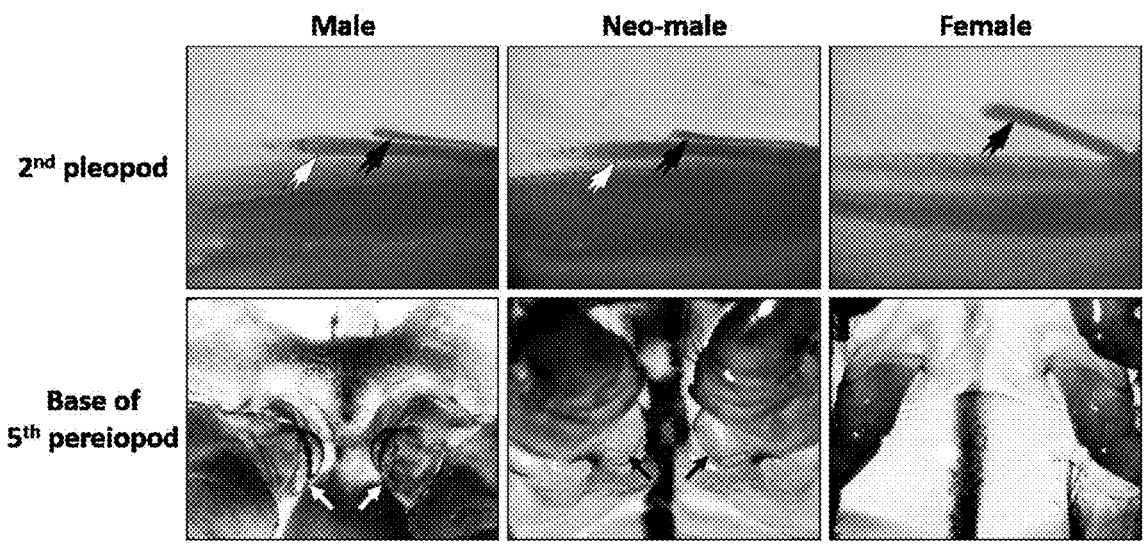
FIG. 7: Micrographs showing *M. rosenbergii* Neo-males develop hallmark male sex characteristics. Single injection of AG cell suspension induces the development of specific sex characteristics restricted to male *M. rosenbergii*: AM on the $2^{nd}$ pleopod (white arrow) and gonopores at the bases of the $5^{th}$ pereiopods (arrows). Morphologically, males (left column) and Neo-males (middle column) are indistinguishable from one another. Females bear only appendix interna (black arrow) and do not develop gonopores at the base of the $5^{th}$ pereiopods (right column).

In total, 210 females which were given a single injection of suspended hypertrophied AG cells were grown for a period of 7-8 months under various conditions (earthen ponds, 3.5 cubic meter tanks, etc.). The vast majority of these manipulated animals were reared in earthen ponds under grow-out conditions, hence examined only once at the final harvest, 9 months from manipulation. One hundred females were found to be completely sex reversed into Neo-males, based the developments of AM and two visible masculine gonopores at the base of the $5^{th}$ pereiopods. Additional females presented partial sex reversal with only some of the male characteristics observed. Additionally, the three distinctive male morphotyps in this species (small male, orange claw and blue claw), were observed. In a more tightly monitored representative group, 16 females (validated according to a genetic sex marker, FIG. 6) were manipulated as above. Approximately 50 days post manipulation, all these 16 genetic females had developed AM, 13 of which have also developed male gonopores (~81%) (FIG. 7, center column) thus, considered as Neo-males. Fourteen (14) intact PL males of the same age as the manipulated females, which have served as references presented both AM and gonopores at the first evaluation point (FIG. 6 and FIG. 7 left column), as expected.

Figure 8:
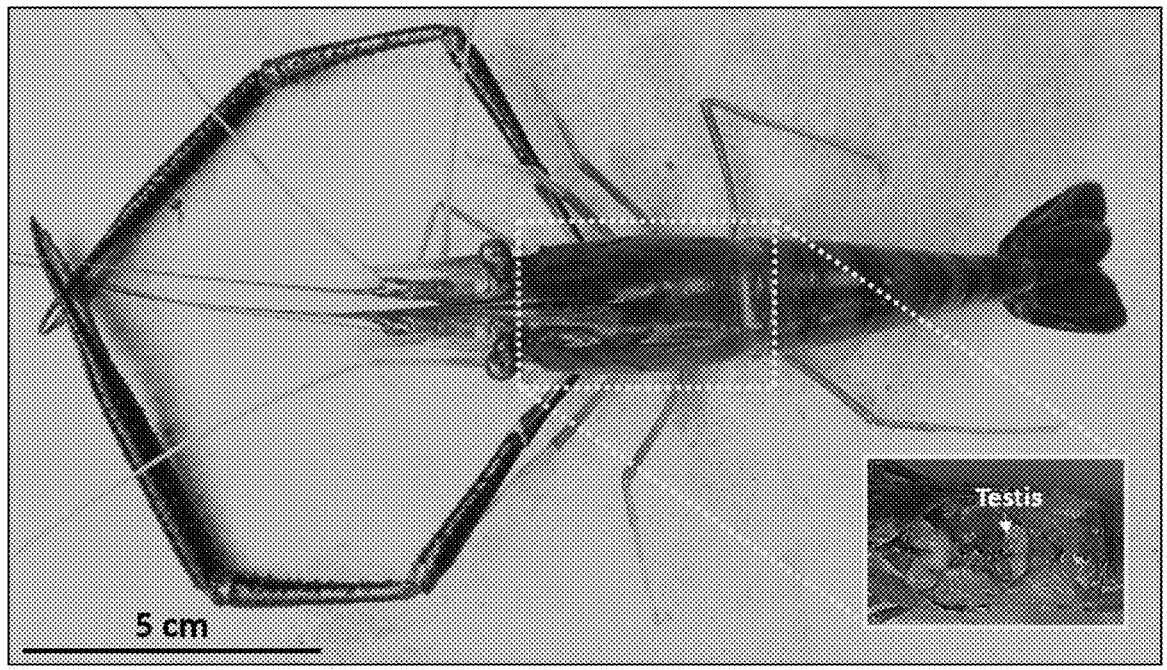
FIG. 8: Micrographs showing *M. rosenbergii* Neo-males achieve full masculine morphotypic differentiation. Neo-males resulting from a single AG cell suspension progressed through normal morphotypic differentiation and developed into fully mature blue-claw, according to conventional measuring system developed by Kuris et al., (1987). The Neo-male's propodus (claw) grew to nearly twice as long as the carapace (70 mm compared with 37 mm, respectively). A large testicular tissue was also observed upon dissection (inset).
Figure 9:
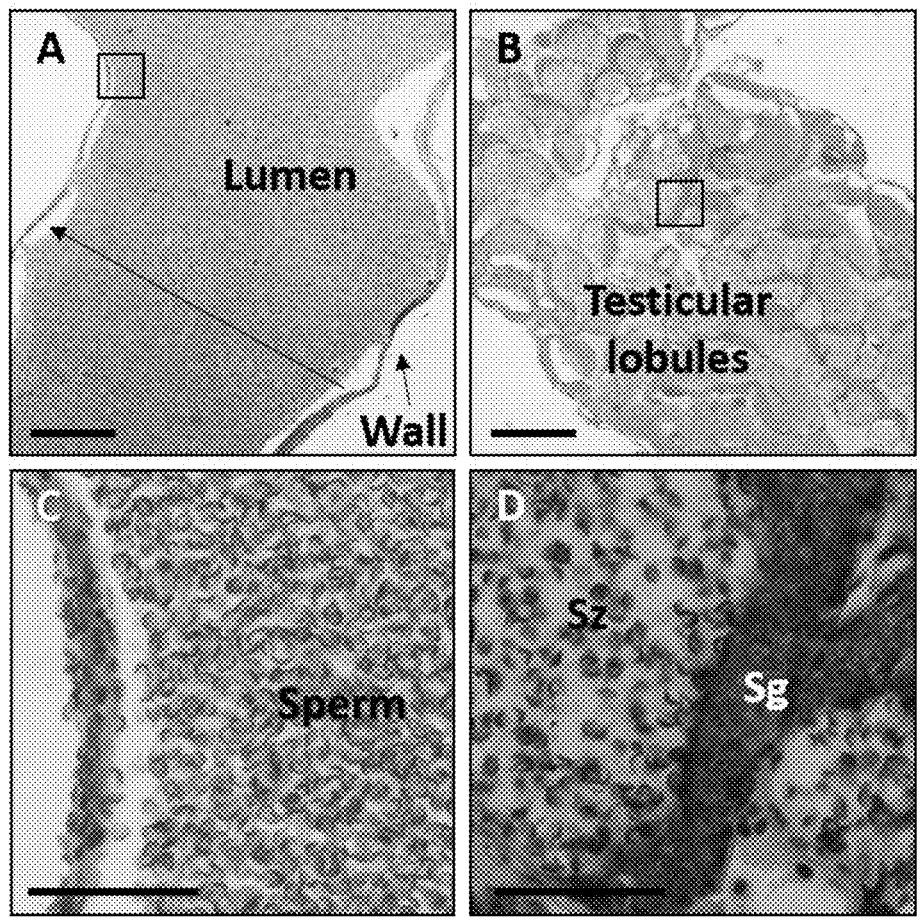
FIG. 9: Micrographs showing *M. rosenbergii* Neo-male shows full masculine gonadogenesis. Histological cross sections stained Hematoxylin and Eosin reveal (A) a sperm-filled sperm duct along with (B) highly active testicular lobules. In the latter highly (dividing)—and lightly (mature)—dense regions were observed. (C) Sperm within the sperm duct showed the characteristic inverted-umbrella morphology of a true Mr mature sperm. (D) Round large spermatogonium (Sg) cells are heavily stained and found to be located in the periphery of a lobule as oppose to spermatozoa (Sz) which were lightly stained and accommodate majority of a lobule's volume, as is the case in sexually reproductive *M. rosenbergii* males. Bar=250 μm (A and B) and 50 μm (C and D). Fields defined in frames in A and B were enlarged and documented as C and D, respectively.

The Neo-males were monitored on a weekly basis and found to retain their AM. Furthermore, Neo-males one year following the manipulation regenerated their AM following a molt regeneration assay. These Neo-males were kept in separate tanks, underwent full morphotypic differentiation and developed into the dominant male morphotype—the 'blue-claw' (a representative individual presented in FIG. 8). With respect to gonadogenesis, blue-claw Neo-males were dissected and their reproductive system comprising mature testes (FIG. 9, inset) were sampled for a histological survey (FIG. 9). The dissected individuals revealed a well-developed sperm duct (FIG. 9A) filled with spermatozoa. Under high magnification the morphology of the cells demonstrated the hallmark structure of the inverted umbrella characterizing this type of mature cells in *M. rosenbergii* males (FIG. 9B).

Furthermore, a well-developed testicular tissue comprised of both highly and lightly stained regions was observed (FIG. 9C). Under high magnification the highly stained regions, located in the periphery of any given lobule, was found to accommodate round dividing spermatogonium cells (FIG. 9D). The lightly stained regions, comprising majority of the lobule's volume were found to accommodate mature spermatozoa.

Example 2

Crossing the Newly Obtained Neo-Males with Normal Females

Mr Neo-males were stocked along with normal females in communal tanks (3.5-10 cubic meters). Once a week, all the females were collected from the tank after which, only egg-berried females were removed into individual glass tanks. The females were monitored daily until eggs' color had changed from orange to gray by which they were transferred to spawning tanks of 12-15 ppt saline water. After hatching, the females were removed and larvae-culture had commenced as customary. To determine whether a female was indeed fertilized by a Neo-male, each progeny were kept separately, and immediately after metamorphosis the gender and genotypic sex of the post larvae were determined as described above.

Figure 10:
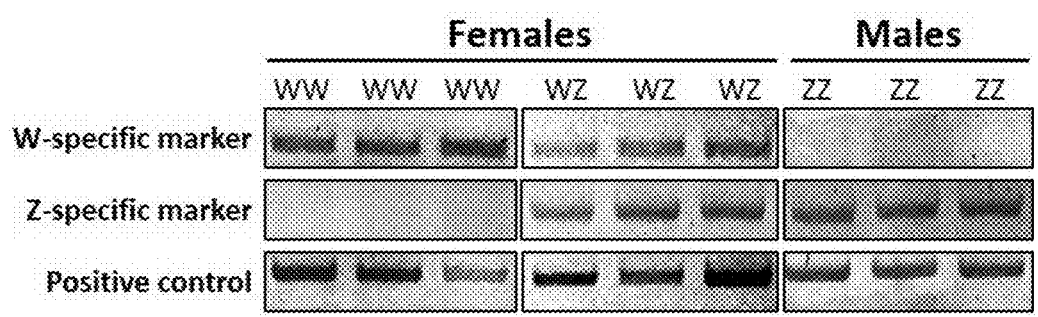
FIG. 10: Molecular progeny test of Neo-male crossed with a normal female: A gel micrograph showing genetic sex determination of selected PLs from the progeny of a Neo-male crossed with a normal female. To discriminate the morphologically-indistinguishable males from females (at the early age of $PL_{20}$), all the representatives were genetically examined using a W-specific DNA sex marker. The latter was amplified by means of PCR and was separated through a 2% agarose gel stained by Ethidium Bromide and visualized using UV (upper panel). To further discriminate the 2 sub-populations of females, WZ and WW, the molecular analysis was performed using a Z-specific DNA sex marker, with males serving as control (middle panel). Mr β-actin served as a positive control for PCR, ensuring the presence of DNA in each sample (lower panel).
Figure 11:
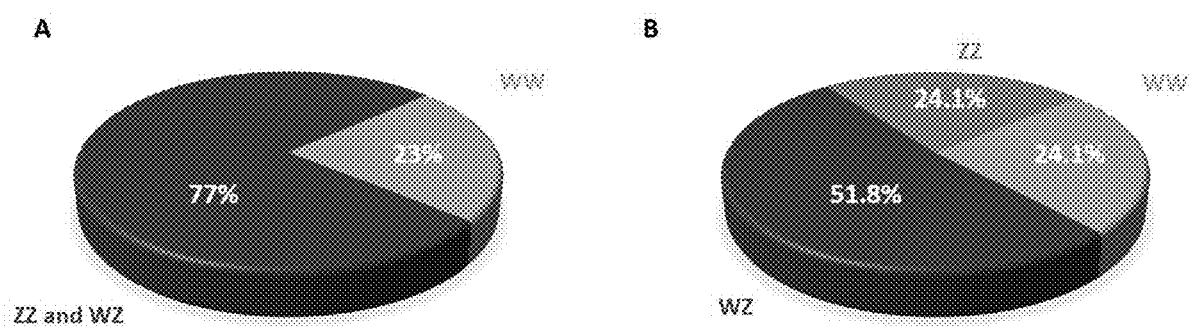
FIG. 11: Pie charts showing genotypic distribution of Neo-male×normal female progeny. The genotypes with respect to genetic sex of PLs from the progeny of a Neo-male and a normal female were determined using the molecular sex markers based on which final distributions were calculated. (A) The total distribution of 865 PLs based on solely the Z-specific sex marker revealed that approximately three quarters of the progeny (77%) is comprised of WZ females and ZZ males. The remaining PLs (23%) are WW females. (B) A representative group of 174 PLs were sampled (from the 865 PLs) and genetically analyzed using both the W- and Z-specific sex markers. The final genotypic sex determination indicated that WW females and ZZ males are at 1:1 ratio (24.1% each) and are both at approximately 1:2.1 ratio with normal WZ females (51.8%).

Females which were stocked along with broodstock Neo-males in communal tanks were successfully fertilized. Upon metamorphosis, PLs were genetically characterized using the DNA sex markers to verify that indeed WW PLs were present (FIG. 10) (thus excluding the possibility the female was fertilized by a normal ZZ male). In total, out of 865 examined individuals representing 4 different crossings of at least 2 different Neo-males, 77% (n=668) were positive for the Z chromosome DNA sex marker, namely, WZ females and ZZ males (FIG. 11A). Consequently, the remaining 23% (n=197) were determined as WW females. Furthermore, both the W and Z chromosomes DNA sex markers were used to comprehensively characterize the precise distribution of genotypes among a sample of 174 PLs. Of the latter, 42 were identified as ZZ males (24.1%), 90 as WZ females (51.8%) and 42 as WW females (24.1%), with a ZZ: WZ: WW genotypic ratio of 1:2.1:1 (FIG. 11B).

Example 3

Crossing on Commercial Scale

P Generation

At the parental generation (P), a single broodstock (Normal ZZ male and WZ female) produced a progeny comprised of 2,000 to 5,000 thousands of WZ siblings.

F1 Generation

Of the latter, 10 randomly chosen first generation (F1) WZ females undergone the sex-reversal manipulation which included cell injection as described herein. At least 5 of the chosen WZ females were successfully sex reversed into fully functional WZ Neo-males. This trial in which 50% success rate was recorded is in accordance to others involving successful sex-reversal of WZ females into Neo-males.

F2 Generation

Each of these Neo-males (sibling) was grown to sexual maturity and was allowed to mate once with a normal WZ female. These crossings gave rise to at least five F2 progenies. Each F2 progeny offspring are related as cousins to a parallel F2 offspring of F2. Within each of the mentioned F2 progenies at least 700 WW females were obtained. Obviously, these WW females could not have been obtained without the sex-reversal manipulation of the WZ females and are therefore not a product of nature.

Each of the F2 WW females obtained from different F2 progenies must be cousins produced from crossings involving at least 5 different F1 Neo-males (which must be F1 Neo-males brothers) originating from the same parents. At least 5 such cousins were obtained, a minimal number required for mass production.

The invention claimed is:

1. A primary cell culture comprising: cell culture medium and cells isolated from a hypertrophied androgenic gland (AG) of a decapod crustacean, wherein at least 85% of said cells within said primary cell culture are endocrine AG cells, and wherein said primary cell culture is devoid of an intact tissue and tissue fragments.

2. The primary cell culture of claim 1, wherein 100% of the cells within said culture are cells isolated from a hypertrophied androgenic gland (AG) of a decapod crustacean.

3. The primary cell culture of claim 1, wherein hypertrophied AG gland is also a hyperplasic AG gland.

4. A composition comprising at least $1\times10^2$ solitary cells isolated from a hypertrophied androgenic gland (AG) of a decapod crustacean.

5. The composition of claim 4, wherein hypertrophied AG gland is also a hyperplasic AG gland.

* * * * *